United States Patent
Hristov et al.

(10) Patent No.: US 7,551,759 B2
(45) Date of Patent: Jun. 23, 2009

(54) TARGET IDENTIFICATION USING TIME-BASED DATA SETS

(75) Inventors: Dimitre Hristov Hristov, Walnut Creek, CA (US); Gangadharan M. Bijumon, Concord, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 782 days.

(21) Appl. No.: 11/007,068

(22) Filed: Dec. 7, 2004

(65) Prior Publication Data

US 2006/0122499 A1 Jun. 8, 2006

(51) Int. Cl.
*G06K 9/00* (2006.01)
*A61B 1/00* (2006.01)

(52) U.S. Cl. ...................... 382/128; 600/425
(58) Field of Classification Search ............. 382/132, 382/131, 130, 254, 255, 266, 154; 378/4–27, 378/11, 13, 7; 250/353.04, 363.05, 455; 356/9, 12–13, 2; 395/118, 119, 120; 128/653.1, 128/922–925; 600/300–301, 425
See application file for complete search history.

(56) References Cited

U.S. PATENT DOCUMENTS

| 5,761,131 A * | 6/1998 | Roohparvar ........... 365/189.02 |
| 5,774,357 A * | 6/1998 | Hoffberg et al. ............. 713/600 |
| 6,780,152 B2 * | 8/2004 | Ustuner et al. .............. 600/443 |

OTHER PUBLICATIONS

George Zubal and Chuck Harrell, "Voxal Based Monte Carlo Calculations of Nuclear Medicine Images and Applied Variance Reduction Techniques", Division of Imaging Science; Department of diagnostic Radiology; Yale University, New Haven, CT 06510; Springer Berlin / Heidelberg, 0302-9743, vol. 511/1991 pp. 23-33.*

* cited by examiner

*Primary Examiner*—Samir A. Ahmed
*Assistant Examiner*—Mehdi Rashidian (57) ABSTRACT

A system includes acquisition of a first image of a portion of a body, the first image representing the portion during a first phase of motion, acquisition of a second image of the portion of the body, the second image representing the portion during a second phase of motion, generation of a composite image based on the first image and the second image, the composite image indicating a position of a target during the first phase of motion and a position of the target during the second phase of motion, and identification of a target region based on the composite image.

35 Claims, 11 Drawing Sheets

TARGET IDENTIFICATION USING TIME-BASED DATA SETS

BACKGROUND

1. Field

The embodiments described below relate generally to imaging, and may be applied to systems for generating time-based images.

2. Description

Three-dimensional imaging systems are commonly used to generate images of an internal portion of a body. As one example, a computed tomography (CT) system includes an X-ray source and a radiation receiver that are mounted to face one another on opposite sides of a ring. A body is positioned within the ring so that a portion of interest lies between the X-ray source and the radiation receiver. The X-ray source then emits X-ray radiation that passes through the portion of interest and is received by the radiation receiver.

The receiver produces a set of data that represents the attenuative properties of tissues that lie between the X-ray source and the receiver. This set of data comprises a projection image. The ring is then rotated in order to rotate the X-ray source and the radiation receiver around the portion of interest. During the rotation, the X-ray source transmits radiation toward the receiver and the receiver produces projection images corresponding to various rotational angle positions. A three-dimensional image of the portion of interest may be generated from the projection images using known reconstruction techniques.

Most reconstruction techniques assume that the spatial distribution of the internal portion's linear attenuation coefficient is identical for all rotational angle positions. This assumption is not accurate if the portion is in motion during acquisition of the projection images. Therefore, to provide improved three-dimensional imaging of a body in periodic motion (e.g., resulting from breathing motion, heart beat, etc.), some imaging systems acquire multiple sets of projection images, wherein each set corresponds to a different phase of the periodic motion. Conventional systems may acquire five to ten of such sets of projection images.

A set of projection images that corresponds to a first phase of the periodic motion may be used to generate a three-dimensional image of the internal portion as it appears during the first phase. Similarly, a set of projection images that corresponds to a second phase of the periodic motion may be used to generate a three-dimensional image of the internal portion as it appears during the second phase.

The plurality of three-dimensional images may be used to identify a tumor or other target within the patient. According to some techniques, a radiation oncologist views a "slice" of each three-dimensional image. Each slice illustrates a same portion of the patient, but at different phases of the periodic motion. The oncologist indicates a location of the target within each slice using a graphical input device. As a result, the location of the target during each represented phase of the periodic motion is known. A treatment region is then determined based on the geometrical union of the indicated locations. Such a procedure may be unsatisfactorily time and resource-consuming, particularly when the number of represented phases is large.

According to other target-identification techniques, an oncologist indicates a location of a target within one slice of a first three-dimensional image representing a first phase of motion. A mathematical transform is then determined between the first three-dimensional image and a second three-dimensional image representing a second phase of motion. The transform is applied to the indicated location to determine a second location of the target within the second three-dimensional image. Next, a second mathematical transform is determined between the second three-dimensional image and a third three-dimensional image representing a third phase of motion. The second transform is applied to the second location to determine a third location of the target within the third three-dimensional image. The process continues for each subsequent phase of motion. This latter technique may be unsatisfactory due to one or more of: the time taken to determine the transforms; inaccuracy of the transforms; the time taken to apply the transforms; and the inability of the transforms to correctly predict subsequent locations of a target.

SUMMARY

To address at least the foregoing, some embodiments provide a system, method, apparatus, and means to acquire a first image of a portion of a body, the first image representing the portion during a first phase of motion, acquire a second image of the portion of the body, the second image representing the portion during a second phase of motion, generate a composite image based on the first image and the second image, the composite image indicating a position of a target during the first phase and a position of the target during the second phase, and identify a target region based on the composite image.

In some aspects, the first image and the second image comprise two-dimensional cross-sectional images of the portion of the body. Further aspects may include acquisition of a third two-dimensional cross-sectional image of a second portion of the body, the third image representing the portion during a third phase of motion, acquisition of a fourth two-dimensional cross-sectional image of the second portion of the body, the fourth image representing the portion during a fourth phase of motion, generation of a second composite image based on the third image and the fourth image, the second composite image indicating a position of the target during the third phase of motion and a position of the target at during the fourth phase of motion, and identification of a second target region based on the second composite image. Moreover, a three-dimensional image of the target region may be generated based on the identified first target region and the identified second target region.

According to additional aspects, a third image of the portion of the body is acquired, the third image representing the portion during a third phase of motion, the composite image is generated based on the first image, the second image and the third image, and the composite image indicates a position of a target during the first phase of motion, a position of the target during the second phase of motion, and a position of the target during the third phase of motion.

Generation of the composite image may include determination of a value for a pixel of the composite image based on values of corresponding pixels of the first image and the second image. Such a determination may include a determination of an average, a maximum, or a minimum value of the corresponding pixels.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the claimed invention and sets forth the best mode contemplated by the inventors for carrying out the claimed invention. Various modifications, however, will remain readily apparent to those in the art.

Figure 1:
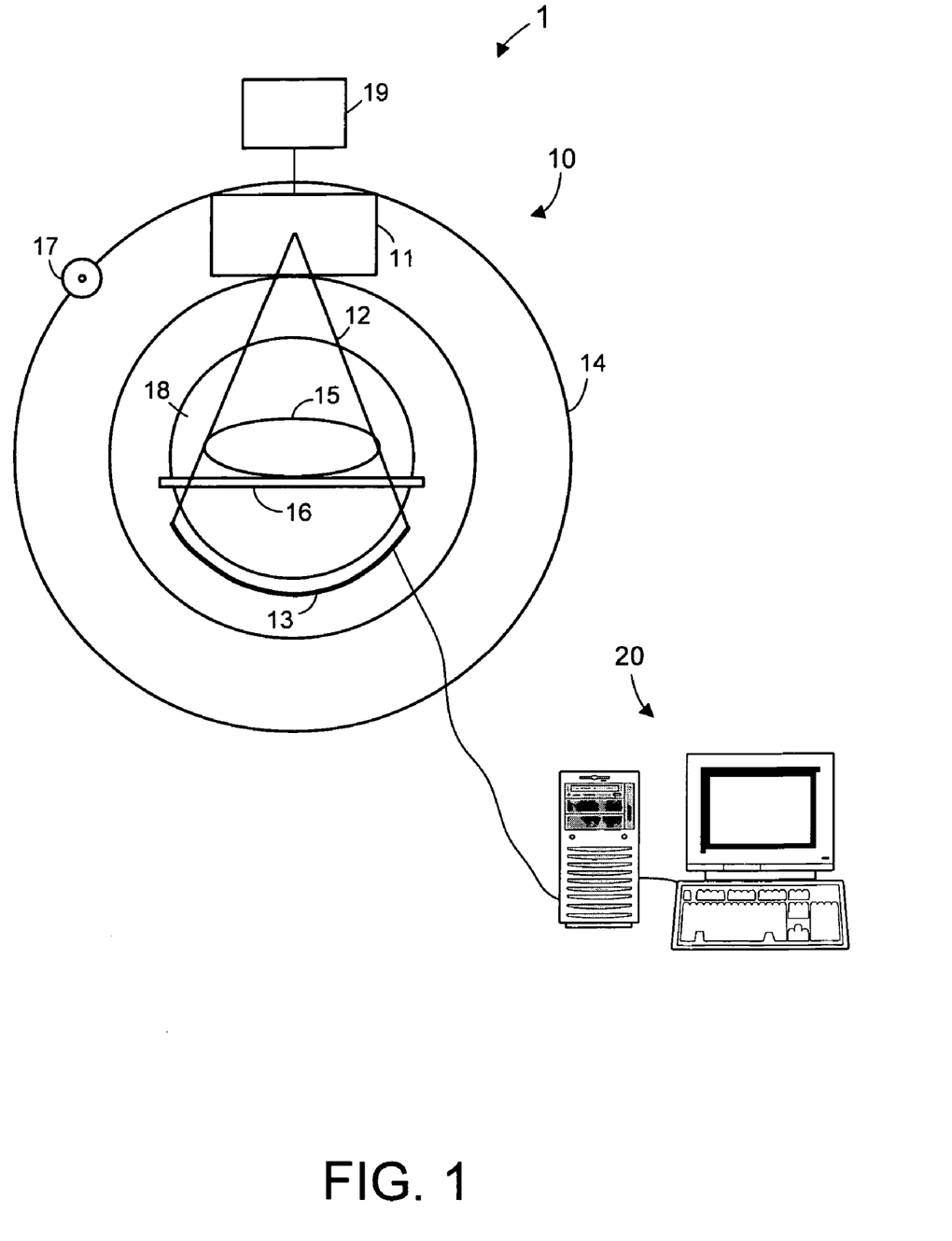
FIG. 1 is a diagram illustrating an image acquisition system according to some embodiments.

FIG. 1 illustrates CT system 1 according to some embodiments. CT system 1 comprises CT scanner 10 and computer system 20. In some embodiments, CT system 1 operates to acquire a first image of a portion of a body, the first image representing the portion during a first phase of motion, and to acquire a second image of the portion of the body, the second image representing the portion during a second phase of motion. In some embodiments, CT system 1 may further operate to generate a composite image based on the first image and the second image, and identify a target region based on the composite image. The composite image may indicate a position of a target during the first phase and a position of the target during the second phase.

CT scanner 10 is located in a CT room and includes X-ray source 11 for emitting fan-shaped X-ray beam 12 toward radiation receiver 13. Both X-ray source 11 and radiation receiver 13 are mounted on ring 14 such that they may be rotated through 360 degrees while maintaining the physical relationship therebetween.

In general operation, body 15 is positioned on bed 16 to place a portion of body 15 between X-ray source 11 and radiation receiver 13. Next, X-ray source 11 and receiver 13 are rotated by rotation drive 17 around cavity 18 in which body 15 lies. During this rotation, X-ray source 11 is powered by high-voltage generator 19 to transmit X-ray radiation toward receiver 13. Receiver 13 receives the radiation and produces a projection image for each projection angle.

The projection images are transmitted to computer system 20. Computer system 20 calculates attenuation coefficients (e.g., Hounsfield numbers) of predetermined points based on the images. The attenuation coefficients may be used to generate an image representing the portion of body 15 that lies between X-ray source 11 and radiation receiver 13. The image may be a three-dimensional image, a two-dimensional cross-sectional ("slice") image, or any other type of image according to some embodiments.

Figure 2:
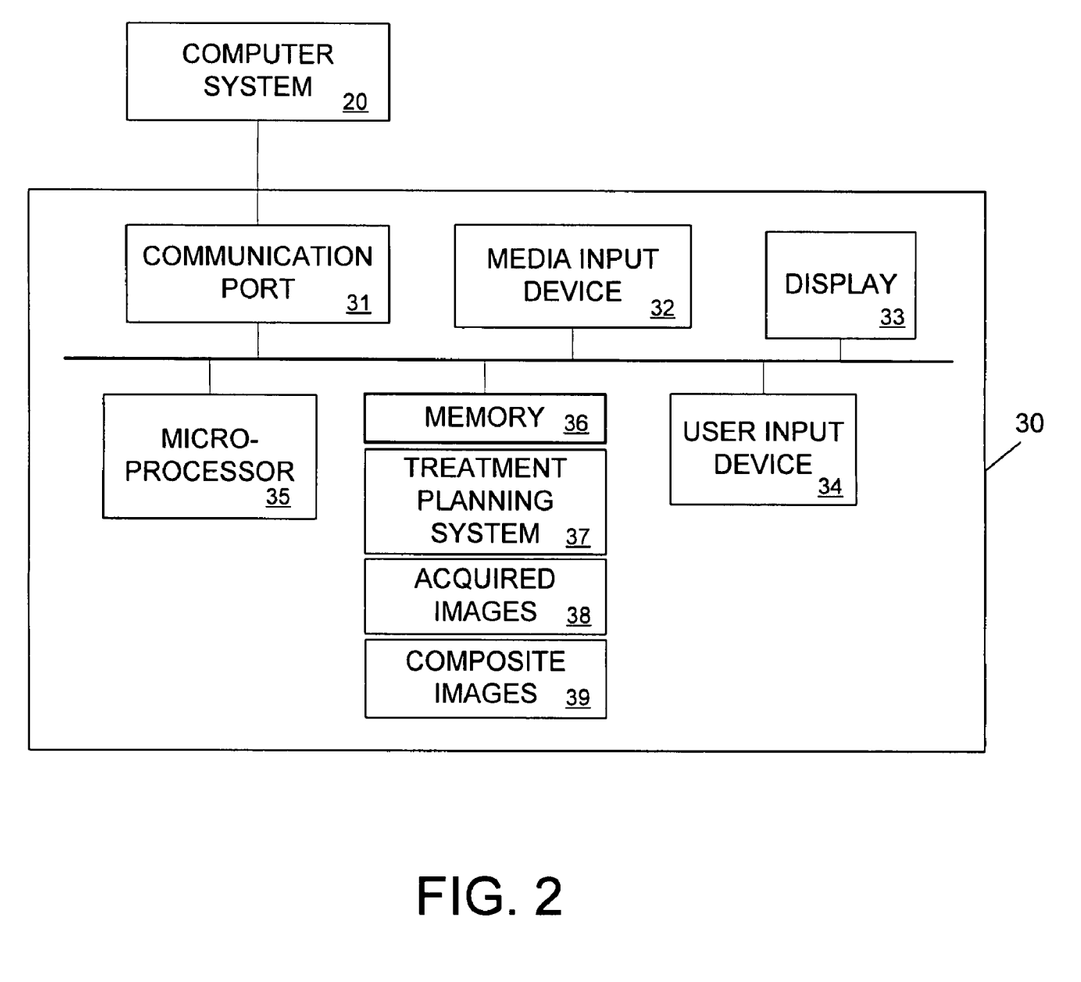
FIG. 2 is a block diagram illustrating elements of an image acquisition system according to some embodiments.

FIG. 2 is a block diagram of treatment planning computer 30 according to some embodiments. Treatment planning computer 30 may operate to generate a composite image based on the above-described first image and second image, and identify a target region based on the composite image. The composite image may indicate a position of a target during the first phase and a position of the target during the second phase.

Treatment planning computer 30 includes communication port 31 for receiving the first image and the second image from computer system 20. Communication port 31 may comprise any type of interface suitable for receiving data from computer system 20. Computer 30 also includes media input device that may comprise a CD-ROM drive, a ZIP drive, a USB drive and/or any device for receiving a storage medium and reading data from the medium.

Display 33 may comprise any one or more devices for displaying images and control interfaces to a user. As will be described below, display 33 may display images such as the first, second and composite images to a user. User input device 34 may be used by the user to input data and commands to computer 30. User input device 34 may comprise any input device or devices that are or become known.

Microprocessor 35 executes processor-executable process steps stored in memory 36. In this regard, memory 36 stores processor-executable process steps of treatment planning system 37. Steps of treatment planning system 37 may be executed by microprocessor 35 to determine a radiation treatment plan based on the acquired images, which are stored among acquired images 38. According to some embodiments, the steps of treatment planning system 37 are executed to generate a composite image based on the image of the portion of the body during the first phase of motion and the image of the portion of the body during the second phase of motion, the composite image indicating a position of a target a during the first phase of motion and a position of the target during the second phase of motion, and to identify a target region based on the composite image. The composite image may be stored among composite images 39 within memory 36.

A hardware environment according to some embodiments may include less or more elements than those shown in FIGS. 1 and 2. In addition, embodiments are not limited to the devices and/or to the illustrated environment. For example, some embodiments include another type of image acquisition device (e.g., a magnetic resonance imager, etc.) to acquire images. According to some embodiments, computer system 20 controls the image acquisition device, generates the composite image, and identifies the target region.

Figure 3:
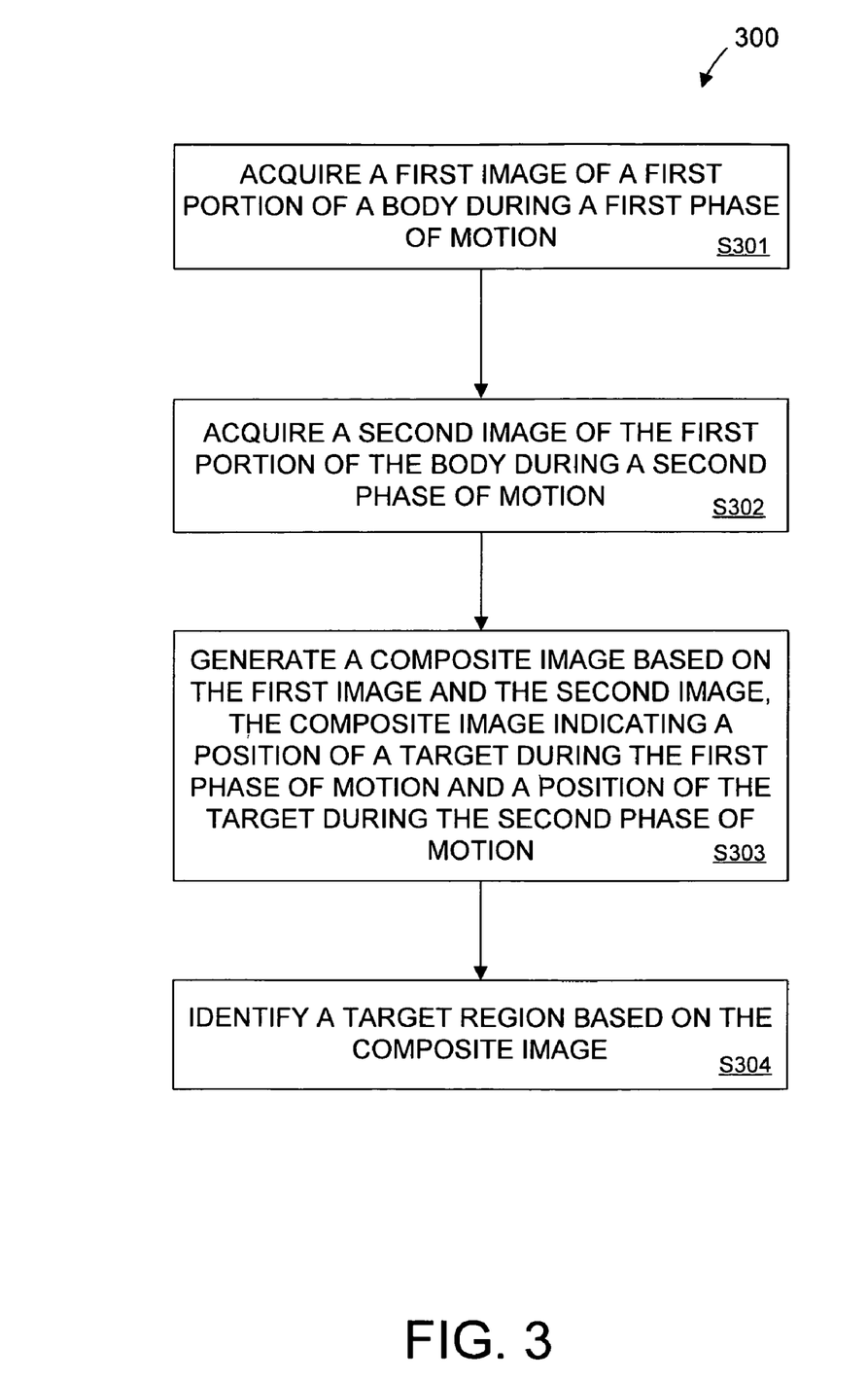
FIG. 3 comprises a flow diagram illustrating process steps according to some embodiments.

FIG. 3 is a flow diagram of process steps 300 executed by system 1 according to some embodiments. Process steps 300 may be embodied, in whole or in part, by hardware of and/or software executed by elements including but not limited to those of CT scanner 10, computer system 20, and treatment planning computer 30. Software embodying process steps 300 may be stored by any medium, including a fixed disk, a floppy disk, a CD-ROM, a DVD-ROM, a Zip™ disk, a magnetic tape, or a signal. Some or all of such software may also be stored in one or more devices.

Initially, at step S301, a first image of a first portion of a body is acquired. The image represents the first portion of the body during a first phase of motion. In some embodiments, the body is a living being undergoing periodic motion due to physiological process such as heartbeat and/or respiration.

The first image may be acquired by operating CT system 1 to acquire projection images of the portion of the body from various projection angles, where each projection image is acquired during a first phase of the body's motion. External monitoring systems may monitor the motion to assist in acquiring each image during the first phase of motion. In this regard, one or more of the projection images may be acquired at different times. A first three-dimensional image may be generated by computer system 20 based on the acquired projection images. The first three-dimensional image therefore represents the portion of the body during the first phase of motion. The first three-dimensional image, as well as the second three-dimensional image described below, may be transmitted from computer system 20 to computer 30 and stored among acquired images 38.

Figure 4:
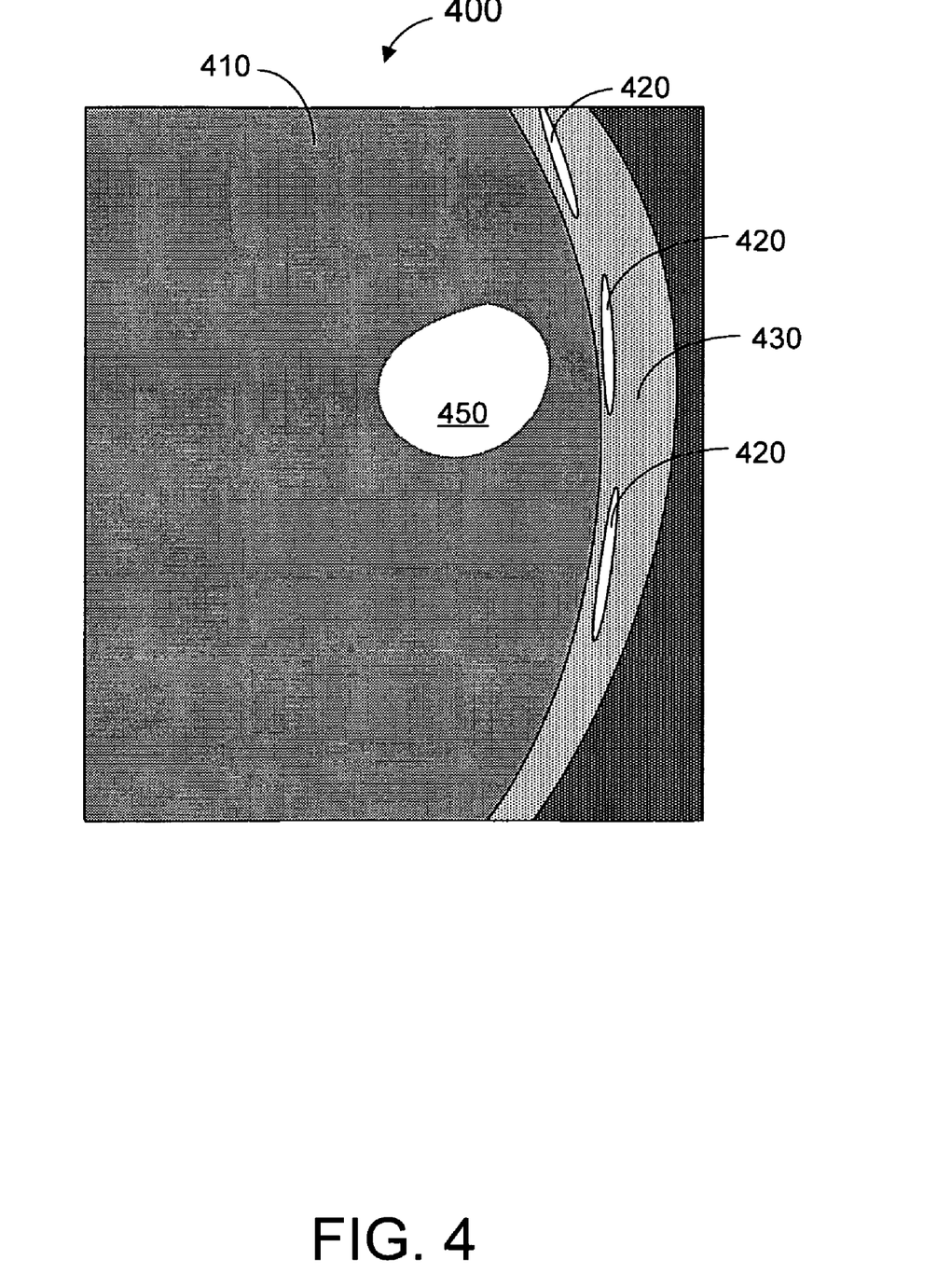
FIG. 4 is a representation of a first image acquired at a first time according to some embodiments.

FIG. 4 represents a two-dimensional cross-sectional image acquired according to some embodiments of step S301. Image 400 may be directly generated from projection images that are acquired as described above, or may be generated from the first three-dimensional image described above. Image 400 represents a portion of a patient's chest, with area 410 representing the chest cavity, areas 420 representing ribs, area 430 representing chest tissue, and area 440 representing areas external to the patient. Area 450 represents a tumor or other target within area 410 during the first phase of motion of the patient.

Next, at step S302, a second image of the first portion of the body is acquired. The second image represents the first portion of the body during a second phase of motion. Similarly to the above description of step S301, acquisition of the second image may include acquisition of projection images of the portion of the body from various projection angles, where each projection image is acquired during the second phase of the body's motion. A second three-dimensional image representing the portion of the body during the second phase of motion may be generated based on the acquired projection images.

Figure 5:
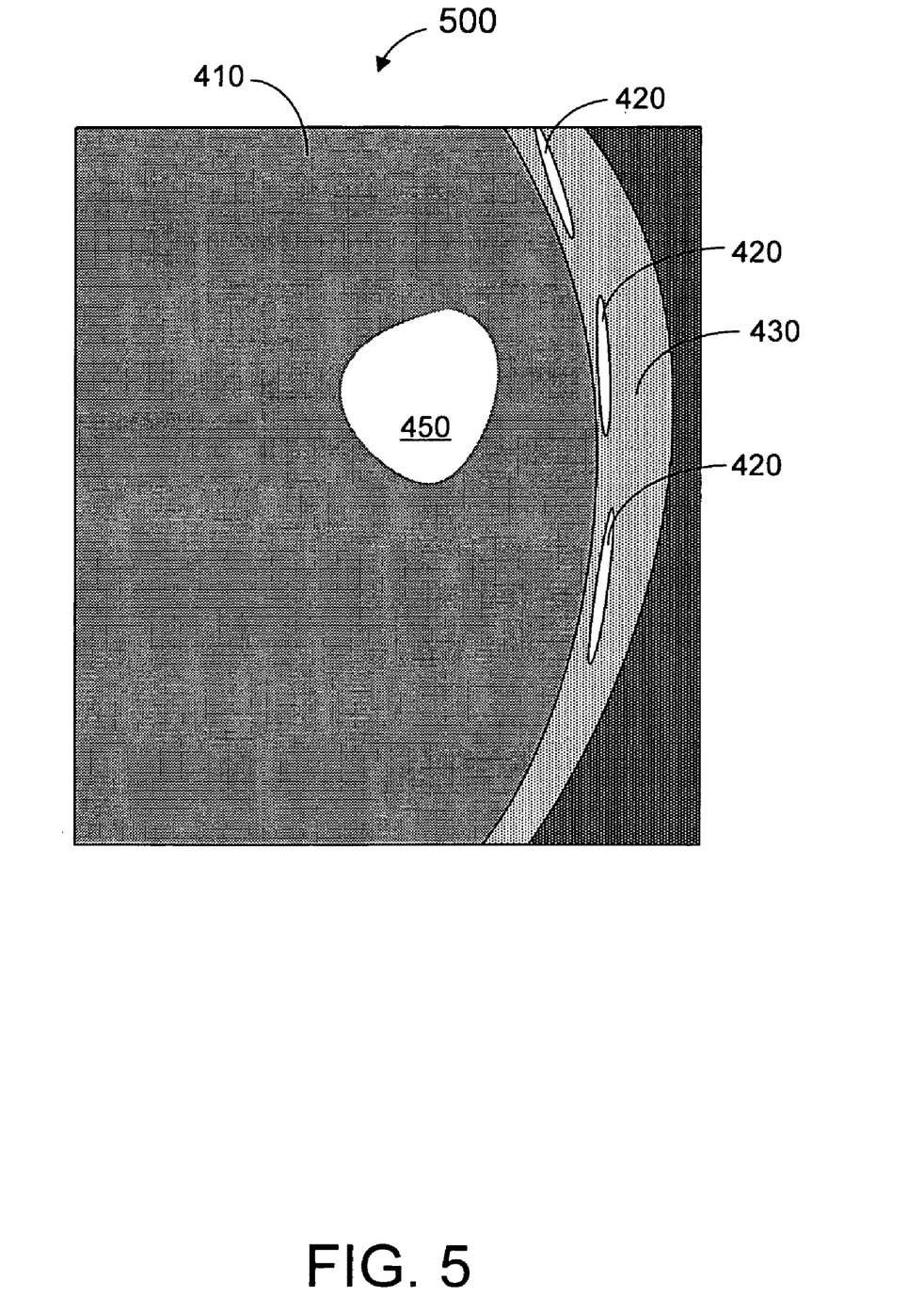
FIG. 5 is a representation of a second image acquired at a second time according to some embodiments.

FIG. 5 represents two-dimensional cross-sectional image 500 according to some embodiments of step S302. Image 500 may be directly generated from projection images that are acquired during step S302, or may be generated from the above-described second three-dimensional image. Image 500 shows areas 410 through 440 during the second phase of motion. As shown, a location and shape of target 450 differs between image 400 and image 500.

Returning to process 300, a composite image is generated at step S303 based on the first image and the second image. According to some embodiments, computer system 30 executes process steps of treatment planning system 37 at step S303 to generate a composite image. The composite image may indicate a position of the target during the first phase of motion and a position of the target during the second phase of motion. Such a composite image may be stored among composite images 39 according to some embodiments. As mentioned above, computer system 20 may be used to generate the composite image according to some embodiments of step S303.

Figure 6:
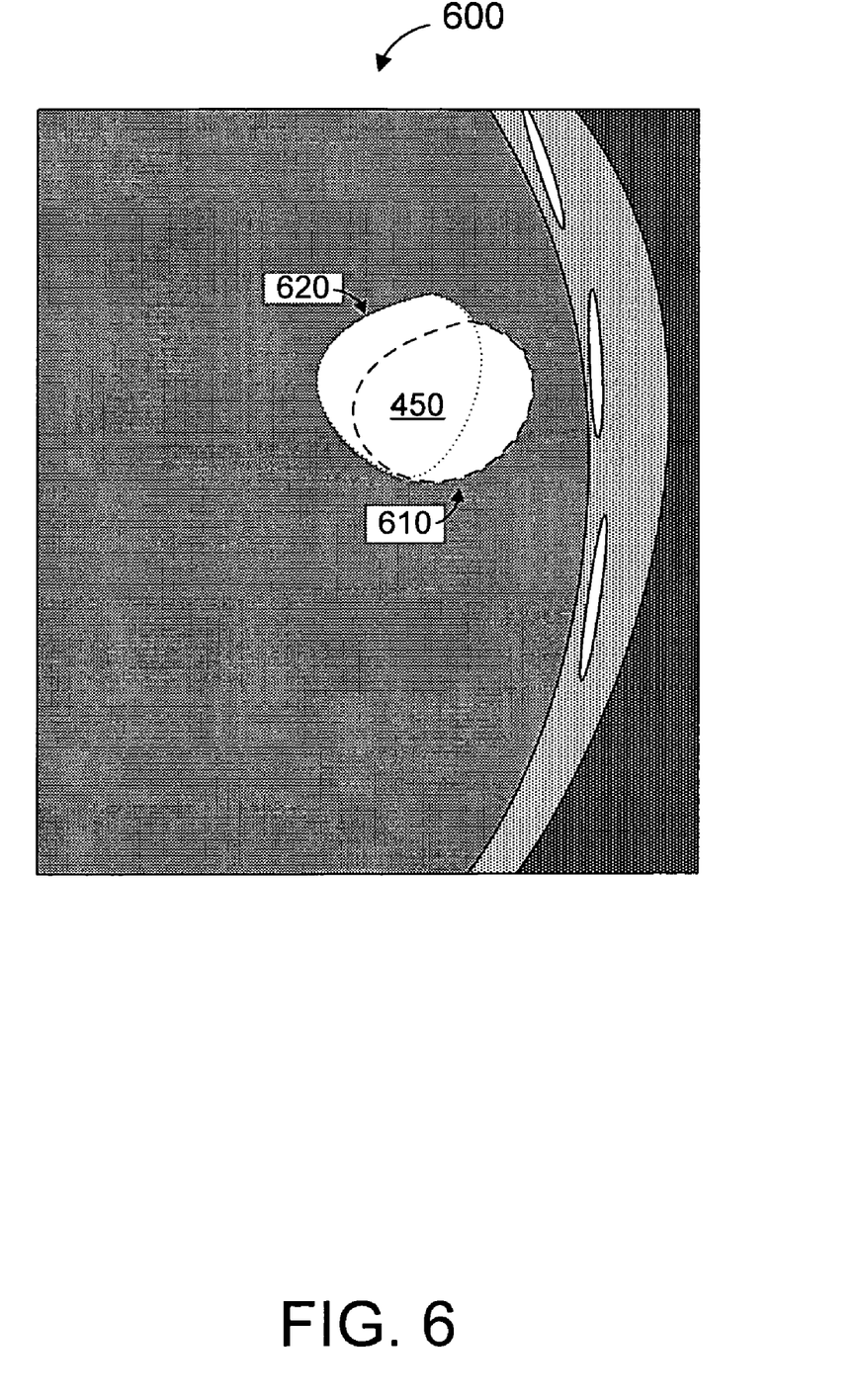
FIG. 6 is a representation of a composite image based on the first and second images according to some embodiments.

FIG. 6 illustrates a composite image according to the present example. Image 600 indicates a location of target 450 during the first phase (as represented in image 400) and a location of target 450 during the second phase (as represented in image 500). In the illustrated embodiment, dashed line 610 indicates the location of target 450 during the first phase and dotted line 620 indicates the location of target 450 during the second phase.

According to some embodiments, the composite image does not include dotted or dashed lines to indicate the target locations during the respective phases. Such embodiments may indicate the target locations using by somehow contrasting the target locations with the background area. One example of this technique would result in a composite image identical to composite image 600, but without lines 610 or 620.

Image 600 may be determined using any currently-or hereafter known method to indicate the above-described two locations. According to some embodiments, a value of each pixel of image 600 is determined based on values of corresponding pixels of image 400 and image 500. For example, a value of a pixel of image 600 is determined to be equal to an average of the values of corresponding pixels of image 400 and image 500. In another example, a value of a pixel of image 600 is determined to be equal to a maximum of the values of corresponding pixels of image 400 and image 500. According to yet another example, a value of a pixel of image 600 is determined to be equal to a minimum of the values of corresponding pixels of image 400 and image 500.

Figure 7:
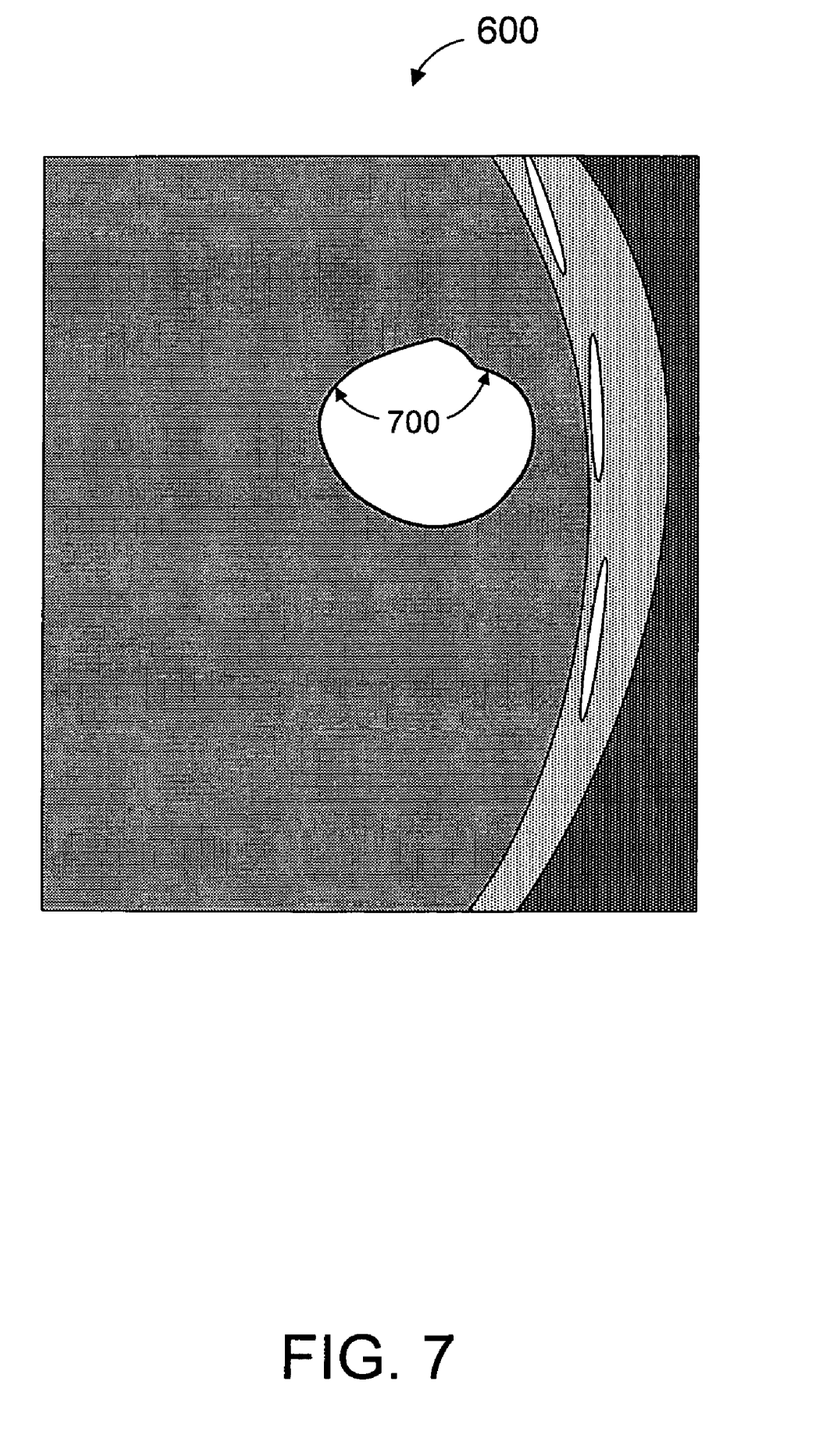
FIG. 7 is a representation of the composite image including an indication of a target region according to some embodiments.

A target region is identified based on the composite image at step S304. Identifying the target region at step S304 may include displaying an overlay over the target region. FIG. 7 illustrates composite image 600 with such an overlay 700 superimposed thereon.

According to some embodiments of step S304, image 600 is displayed on display 33 of computer system 30. A user such as a radiation oncologist views image 600 and operates user input device 34 to indicate a target region within image 600. Computer system 30 receives the user input indicating the target region and displays overlay 700 in response thereto.

Figure 8A:
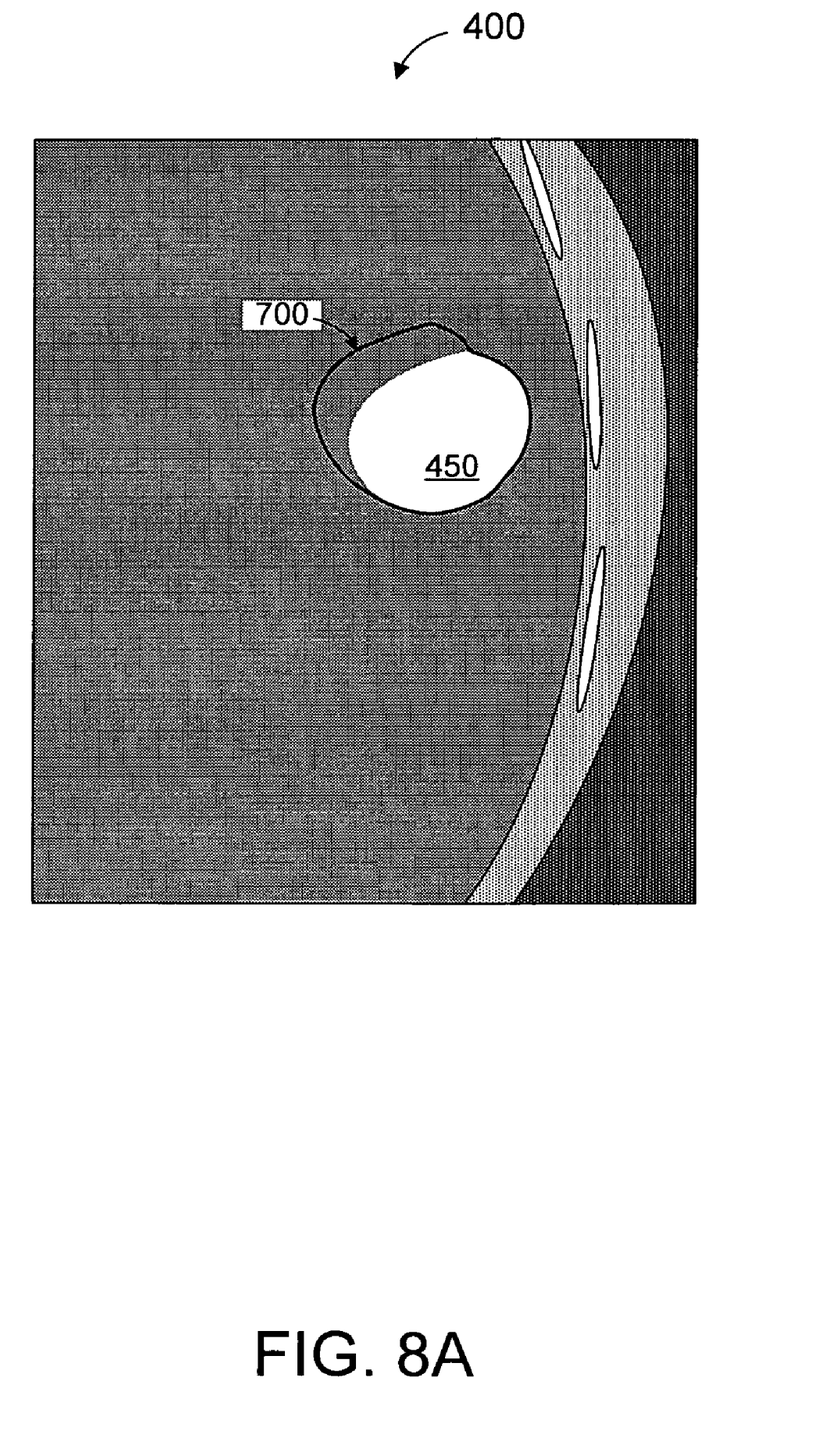
FIG. 8A is a representation of the first image including the indication of the target region according to some embodiments.
Figure 8B:
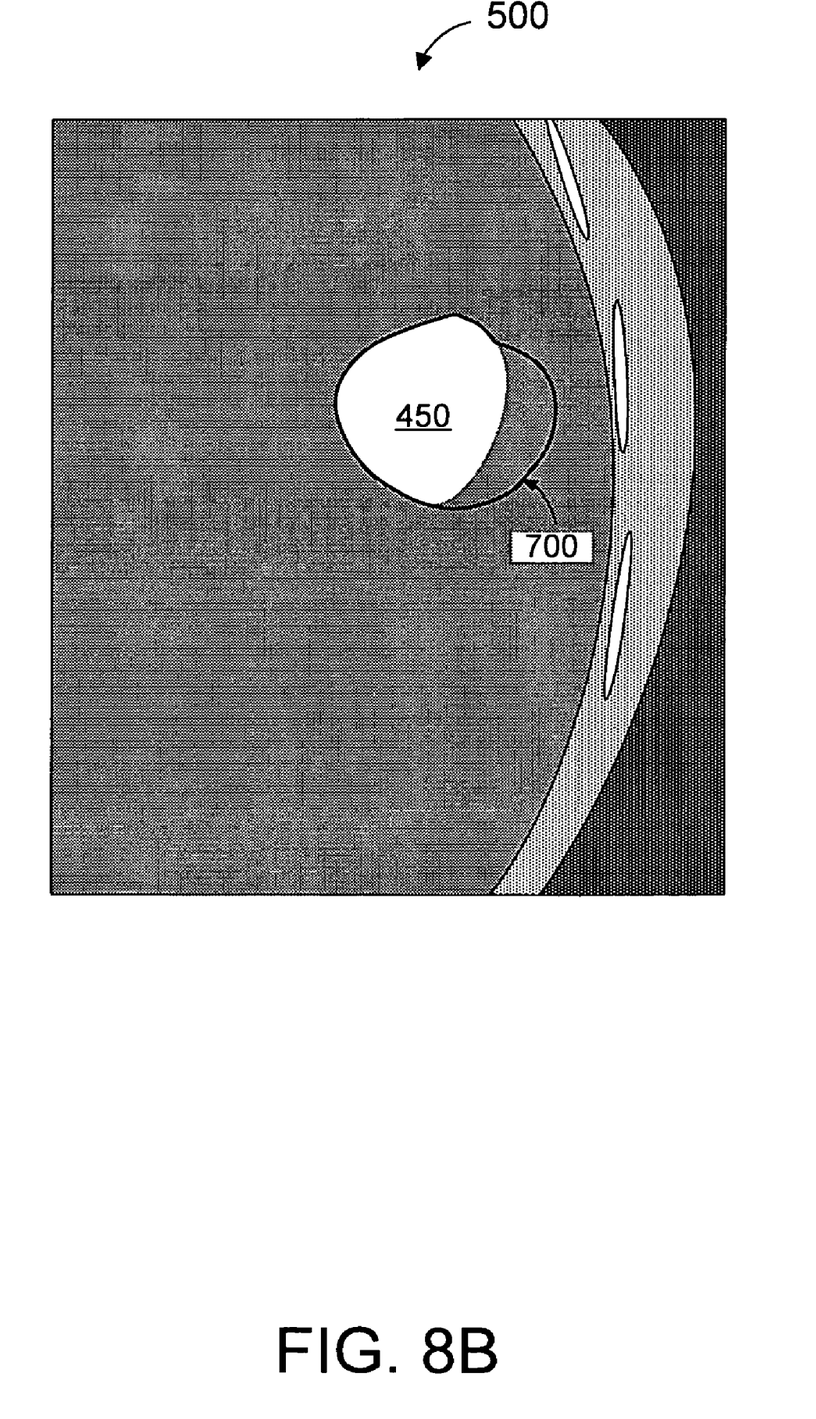
FIG. 8B is a representation of the second image including the indication of the target region according to some embodiments.

Overlay 700 may be used by process steps of treatment planning system 37 to identify a location of a target region to which treatment radiation should be applied. The location of the target region may be confirmed in some embodiments by superimposing overlay 700 on the first image and the second image acquired in steps S301 and S302, respectively. FIG. 8A illustrates image 400 having overlay 700 superimposed thereon, and FIG. 8B illustrates image 500 having overlay 700 superimposed thereon. Images such as those illustrated in FIGS. 8A and 8B may be displayed on display 33 to confirm the delineation of the target region with respect to the location of target 450 as represented in each acquired image.

According to some embodiments of process 300, images of the body may be acquired during any number of phases. A composite image that is generated based on such images may indicate a position of the target during each of the any number of phases. For example, a third image of the first portion may be acquired during a third phase of motion and between steps S302 and S303. The third image represents the first portion of the body during the third phase of motion. The composite image may therefore be generated in step S303 based on the first image, the second image and the third image. A value of each pixel of the composite image is then determined based on values of corresponding pixels of the first image, the second image, and the third image. Consequently, the composite image will indicate a position of the target during the first phase, a position of the target during the second phase, and a position of the target during the third phase.

In some embodiments, steps S301 through S304 may be repeated with respect to a second portion of the body. The second portion may be adjacent to the first portion. Referring back to the above example, the second portion may lie in a plane parallel to the plane of images 400 through 600 and may be located just behind or just in front of the plane of images 400 through 600. The second portion may alternatively lie in a plane perpendicular or otherwise skew to the plane of images 400 through 600.

Therefore, some embodiments may acquire a first image of the second portion during the first phase of motion, and a second image of the second portion during the second phase of motion. The images may comprise two-dimensional cross-sectional images that are derived, respectively, from a previously-acquired three-dimensional image of the first portion and the second portion during the first phase and a previously-acquired three-dimensional image of the first portion and the second portion during the second phase. A second composite image may then be generated based on the images of the second portion, where the second composite image indicates a position of the target within the second portion during the first phase of motion and a position of the target within the second portion during the second phase of motion. A second target region is identified in step S304 based on the second composite image. In some embodiments, a three-dimensional image of the target region may be generated based on the identified target region of the first portion and the identified target region of the second portion.

Figure 9:
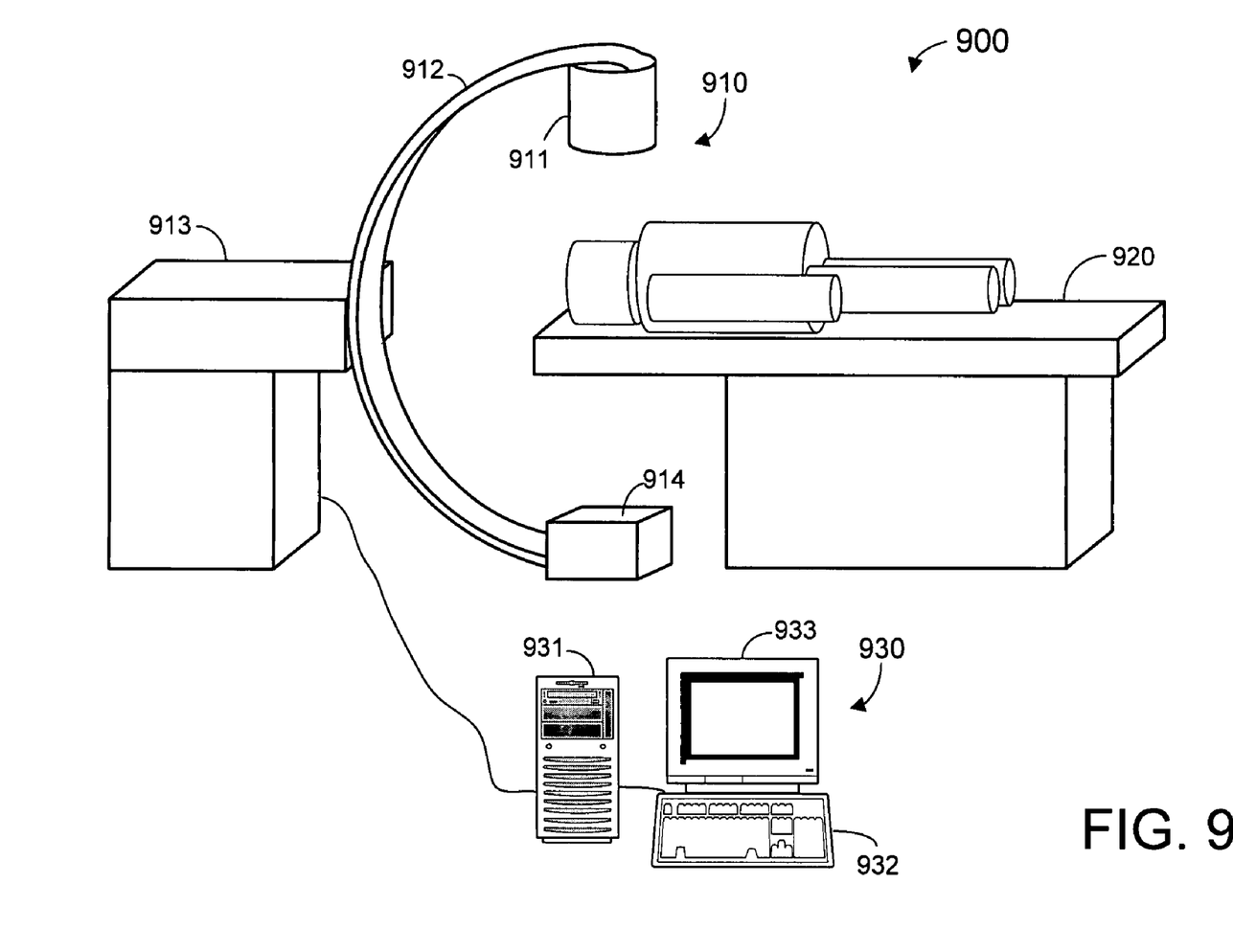
FIG. 9 is a diagram illustrating an image acquisition system according to some embodiments.

FIG. 9 illustrates system 900 to perform process 300 according to some embodiments. System 900 includes kilovoltage imaging system 910, table 920 and operator station 930. Imaging system 910 comprises X-ray tube 911, C-arm 912, base 913 and imaging device 914. X-ray tube 911 may comprise any suitable device to emit imaging radiation, and, in some embodiments, emits kilovoltage radiation having energies ranging from 50 to 150 keV. Imaging device 914 may comprise a flat-panel imaging device or any other suitable type of imaging device.

X-ray tube 911 and imaging device 914 may be coupled to C-arm 912 so as to face one another irrespective of any movement of C-arm 912 with respect to base 913. In this regard, C-arm 912 is slidably mounted on base 913 and can therefore be moved in order to change the position of X-ray tube 911 with respect to body 915. Such movement may allow system 110 to acquire projection images from various projection angles around a portion of body 15. These projection images may be used to generate three-dimensional images of the portion as described above. Many C-arm/base configurations may be used in conjunction with some embodiments, including configurations in which base 913 is rotatably mounted to a ceiling of a room containing system 900, configurations in which one C-arm is slidably mounted on another C-arm, and configurations incorporating multiple independent C-arms.

Table 920 supports body 915 during imaging. Table 920 may be adjustable to assist in positioning a portion of the body between X-ray tube 911 and imaging device 914. Operator station 930 includes processor 931 in communication with an input device such as keyboard 932 and operator display 933. An operator may operate operator station 930 to acquire a first image of a portion of a body during a first phase of motion, and to acquire a second image of the portion of the body during a second phase of motion according to some embodiments. Treatment planning computer 30 or operator station 930 may then be used to generate a composite image, display the composite image, and identify a target region in the composite image as described above with respect to process 300.

Figure 10:
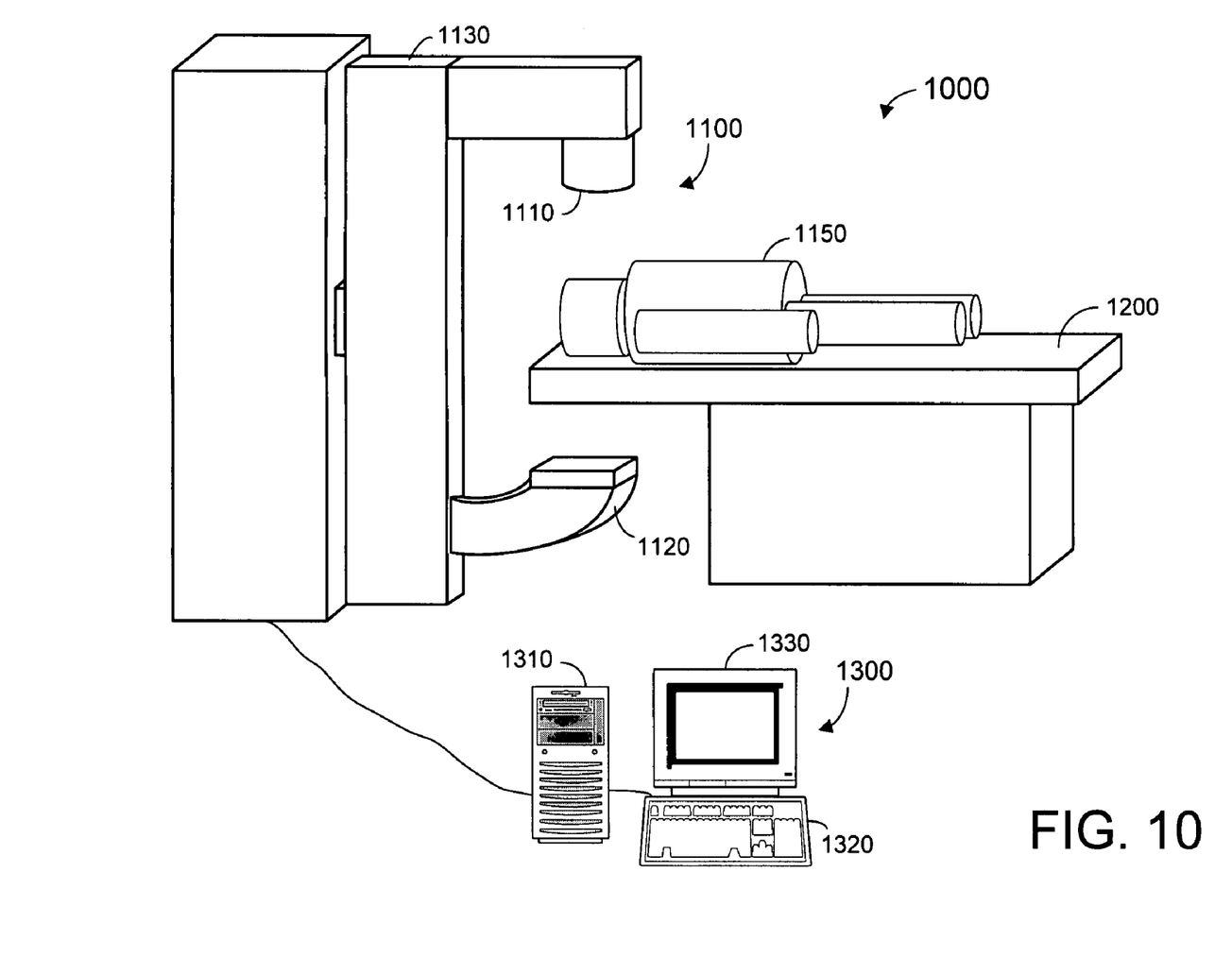
FIG. 10 is a diagram illustrating an image acquisition/radiation treatment system according to some embodiments.

FIG. 10 illustrates system 1000 to execute process steps 300 according to some embodiments. System 1000 includes linear accelerator 1100, table 1200 and operator station 1300. Linear accelerator 1100 may be used to deliver treatment radiation to an identified target region as well as radiation used to acquire images according to some embodiments.

Linear accelerator 1100 comprises treatment head 1110, imaging device 1120, and gantry 1130. Examples of linear accelerators that may be suitable in some embodiments include the PRIMUS® and ONCOR® systems offered by Siemens Corporation®.

Gantry 1130 of linear accelerator 1100 may be rotated to dispose treatment head 1110 and imaging device 1120 at different rotational positions with respect to a portion of body 1150 lying therebetween. Gantry 1130 may be rotated continuously while imaging radiation is emitted from treatment head 1110 during an imaging mode, and may be fixed at a particular rotational position when treatment radiation is emitted from treatment head 1110.

Table 1200 supports body 1150 during imaging and/or radiation treatment. Table 1200 may be adjustable to assist in positioning a desired portion of body 1150 between treatment head 1110 and imaging device 1120. An operator may operate operator station 1300 to acquire images according to some embodiments. Operator station 1300 or treatment planning computer 30 may be used to generate a composite image, display the composite image, and identify a target region in the composite image as described above with respect to process 300.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
    using a processor to perform the steps of: acquiring a first image of a portion of a body, the first image representing the portion during a first phase of motion;
    acquiring a second image of the portion of the body, the second image representing the portion during a second phase of motion;
    generating a composite image based on the first image and the second image, the composite image indicating a position of a target during the first phase of motion and a position of the target during the second phase of motion;
    identifying a target region based on the composite image;
    confirming a location of the target region to apply radiation by:
        superimposing an overlay over a first image portion of the composite image;
        superimposing the overlay over a second image portion of the composite image; and
        determining a delineation of the target region based on the superimposed overlay over the first image portion and the superimposed overlay over the second image portion.

2. A method according to claim 1, wherein the first image and the second image comprise two-dimensional cross-sectional images of the portion of the body.

3. A method according to claim 2, wherein the first and second images are acquired by a computed tomography scanner.

4. A method according to claim 2, wherein the first and second images are acquired using a linear accelerator.

5. A method according to claim 2, further comprising:
    acquiring a third two-dimensional cross-sectional image of a second portion of the body, the third image representing the portion during a third phase of motion;
    acquiring a fourth two-dimensional cross-sectional image of the second portion of the body, the fourth image representing the portion during a fourth phase of motion;
    generating a second composite image based on the third image and the fourth image, the second composite image indicating a position of the target during the third phase of motion and a position of the target during the fourth phase of motion; and identifying a second target region based on the second composite image.

6. A method according to claim 5, further comprising:

generating a three-dimensional image of the target region based on the identified first target region and the identified second target region.

7. A method according to claim 5, wherein the first phase of motion is identical to the third phase of motion, and wherein the second phase of motion is identical to the fourth phase of motion.

8. A method according to claim 1, wherein the first image and the second image comprise three-dimensional images of the portion of the body.

9. A method according to claim 8, wherein the composite image comprises a two-dimensional cross-sectional image of the portion of the body.

10. A method according to claim 1, wherein the first and second images comprise projection images of the portion of the body.

11. A method according to claim 1, wherein identifying the target region comprises:

receiving input from a user, the input indicating the target region.

12. A method according to claim 1, further comprising:

acquiring a third image of the portion of the body, the third image representing the portion during a third phase of motion, wherein the composite image is generated based on the first image, the second image and the third image, the composite image indicating a position of the target during the first phase of motion, a position of the target during the second phase of motion, and a position of the target during the third phase of motion.

13. A method according to claim 1, wherein generating the composite image comprises:

determining a value for a pixel of the composite image based on values of corresponding pixels of the first image and the second image.

14. A method according to claim 13, wherein determining the value for the pixel comprises:

determining an average value of the corresponding pixels of the first image and the second image.

15. A method according to claim 13, wherein determining the value for the pixel comprises:

determining a maximum value of the corresponding pixels of the first image and the second image.

16. A method according to claim 13, wherein determining the value for the pixel comprises:

determining a minimum value of the corresponding pixels of the first image and the second image.

17. A method according to claim 1, further comprising:

acquiring n images of the portion of the body, the n images representing the portion during each of n phases of motion, wherein generating the composite image determining a value for a pixel of the composite image based on values of corresponding pixels of the first image, the second image and the n images.

18. A method according to claim 17, wherein determining the value for the pixel comprises:

determining an average value of the corresponding pixels of the first image, the second image and the n images.

19. A method according to claim 17, wherein determining the value for the pixel comprises:

determining a maximum value of the corresponding pixels of the first image, the second image and the n images.

20. A method according to claim 17, wherein determining the value for the pixel comprises:

determining a minimum value of the corresponding pixels of the first image, the second image and the n images.

21. An apparatus comprising:

a memory storing processor-executable process steps; and a processor in communication with the memory and operative in conjunction with the stored process steps to:

generate a composite image based on a first image of a portion of a body, the first image representing the portion during a first phase of motion and a second image of the portion of the body, the second image representing the portion during a second phase of motion, the composite image indicating a position of a target during the first phase of motion and a position of the target during the second phase of motion;

identify a target region based on the composite image; and confirm a location of the target region to apply radiation by superimposing an overlay over a first image portion of the composite image, superimposing the overlay over a second image portion of the composite image, and determining a delineation of the target region based on the superimposed overlay over the first image portion and the superimposed overlay over the second image portion.

22. An apparatus according to claim 21, the processor further operative in conjunction with the stored process steps to:

acquire the first image; and acquire the second image.

23. An apparatus according to claim 21, wherein the first image and the second image comprise two-dimensional cross-sectional images of the portion of the body.

24. An apparatus according to claim 23, the processor further operative in conjunction with the stored process steps to:

acquire a third two-dimensional cross-sectional image of a second portion of the body, the third image representing the portion during a third phase of motion;

acquire a fourth two-dimensional cross-sectional image of the second portion of the body, the fourth image representing the portion during a fourth phase of motion;

generate a second composite image based on the third image and the fourth image, the second composite image indicating a position of the target during the third phase of motion and a position of the target during the fourth phase of motion; and identify a second target region based on the second composite image.

25. An apparatus according to claim 24, the processor further operative in conjunction with the stored process steps to:

generate a three-dimensional image of the target region based on the identified first target region and the identified second target region.

26. An apparatus according to claim 21, wherein the first image and the second image comprise three-dimensional images of the portion of the body.

27. An apparatus according to claim 26, wherein the composite image comprises a two-dimensional cross-sectional image of the portion of the body.

28. An apparatus according to claim 21, wherein the first and second images comprise projection images of the portion of the body.

29. An apparatus according to claim 21, wherein identification of the target region comprises:

reception of input indicating the target region from a user.

30. An apparatus according to claim 21, the processor further operative in conjunction with the stored process steps to:

generate the composite image based on the first image, the second image and a third image of the portion of the body, the third image representing the portion during a third phase of motion, the composite image indicating a position of the target during the first phase of motion, a position of the target during the second phase of motion, and a position of the target during the third phase of motion.

31. An apparatus according to claim 21, wherein generation of the composite image comprises:

determination of a value for a pixel of the composite image based on values of corresponding pixels of the first image and the second image.

32. An apparatus according to claim 31, wherein determination of the value for the pixel comprises:

determination of an average value of the corresponding pixels of the first image and the second image.

33. An apparatus according to claim 31, wherein determination of the value for the pixel comprises:

determination of a maximum value of the corresponding pixels of the first image and the second image.

34. An apparatus according to claim 31, wherein determination of the value for the pixel comprises:

determination of a minimum value of the corresponding pixels of the first image and the second image.

35. An apparatus according to claim 21, wherein generation of the composite image comprises:

determination of a value for a pixel of the composite image based on values of corresponding pixels of the first image, the second image and n images of the portion of the body, the n images representing the portion during each of n phases of motion.

* * * * *